United States Patent [19]

Sekiya et al.

[11] Patent Number: 5,847,243
[45] Date of Patent: Dec. 8, 1998

[54] PROCESS FOR PRODUCING FLUORINATED ALKENE AND FLUORINATED ALKANE

[75] Inventors: Akira Sekiya, Tsukuba; Toshiro Yamada, Edogawa; Kazunori Watanabe, Kawasaki, all of Japan

[73] Assignees: Japan as represented by Director General of the Agency of Industrial Science and Technology; Nippon Zeon Co. Ltd., both of Tokyo, Japan

[21] Appl. No.: 765,624

[22] PCT Filed: Jun. 30, 1995

[86] PCT No.: PCT/JP95/01313

§ 371 Date: Dec. 27, 1996

§ 102(e) Date: Dec. 27, 1996

[87] PCT Pub. No.: WO96/00707

PCT Pub. Date: Jan. 11, 1996

[30] Foreign Application Priority Data

Jun. 30, 1994 [JP] Japan .................................. 6-170385

[51] Int. Cl.$^6$ .................................................. C07C 17/00
[52] U.S. Cl. ............................................. 570/160; 570/161
[58] Field of Search ...................................... 570/160, 161

[56] References Cited

U.S. PATENT DOCUMENTS

| | | | |
|---|---|---|---|
| 2,449,233 | 9/1948 | Kischitz et al. | 570/160 |
| 2,459,783 | 1/1949 | McBee et al. | |
| 3,024,290 | 3/1962 | Henne et al. | |
| 4,902,839 | 2/1990 | Bielefeldt et al. | 570/175 |
| 4,954,666 | 9/1990 | Bielefeldt et al. | |
| 5,084,199 | 1/1992 | Anton | |

FOREIGN PATENT DOCUMENTS

| | | |
|---|---|---|
| 39 35 493 | 5/1991 | Germany . |
| 6-271490 | 9/1994 | Japan . |
| 1070891 | 6/1967 | United Kingdom . |

OTHER PUBLICATIONS

Henne et al, Journal of the American Chemical Society, vol. 67, Aug. 9, 1945, No. 8, pp. 1234–1237.

*Primary Examiner*—John Kight
*Assistant Examiner*—Garth M. Dahlen
*Attorney, Agent, or Firm*—Armstrong, Westerman, Hattori, McLeland & Naughton

[57] ABSTRACT

A vic-dichloro-fluorinated alkene of the formula: $R^1$—CCl=CCl—$R^2$, and a fluorinated alkane of the formula: $R^1$—$CR^3R^4$—$CR^5R^6$—$R^2$, wherein each of $R^1$ and $R^2$ independently represents a perfluoroalkyl group or both of $R^1$ and $R^2$ form together a perfluoroalkylene group, and $R^3$, $R^4$, $R^5$ and $R^6$ independently represent hydrogen or fluorine, are produced from an inexpensive raw material. More specifically, hexachlorocyclopentadiene is reacted with gaseous chlorine using an antimony catalyst, and then the reaction product is reacted with hydrogen fluoride to give 1,2-dichlorohexafluorocyclopentene. Thus-obtained compound is either (i) hydrogenated, or (ii) treated with a fluorinating agent to substitute the chlorine atoms by fluorine atoms, and then hydrogenated, to give the intended fluorinated alkane.

24 Claims, No Drawings

PROCESS FOR PRODUCING FLUORINATED ALKENE AND FLUORINATED ALKANE

TECHNICAL FIELD

This invention relates to a novel process for producing a vic-dichloro-fluorinated alkene having chlorine atoms bonded to carbon atoms of the unsaturated bond, and a process for preparing a fluorinated alkane through the vic-dichloro-fluorinated alkene as an intermediate.

BACKGROUND ART

Halogenated hydrocarbons containing fluorine have heretofore been used as detergents, cooling mediums and others. In recent years, to cope with problem of the damage of the global environment, international restriction on the use of chlorine-containing fluorinated hydrocarbons is now being tightened, and thus, there is an increasing demand for substitutes therefor. Especially fluorinated alkane derivatives containing no chlorine attract attention in view of protection of the environment because they invite no destruction of the ozone layer.

For example, fluorinated alkanes represented by the following formula:

wherein $R^1$ and $R^2$ independently represent a perfluoroalkyl group or may form a perfluoroalkylene group together, and $R^3$, $R^4$, $R^5$ and $R^6$ independently represent a hydrogen or fluorine atom, are expected widely for uses such as detergents, solvents, propellants, heating mediums for heat pumps and others. As specific examples of the fluorinated alkanes, there can be mentioned 1,1,2,2,3,3-hexafluorocyclopentane disclosed as being useful for a detergent in U.S. Pat. No. 5,084,199, and 1,2,3,3,4,4,5,5-octafluorocyclopentane is disclosed as being useful for a detergent and a desiccating agent in Japanese Patent Application No. 5-88022.

Now there is an urgent request for establishment of a process for producing in a commercial scale fluorinated alkanes as substitutes for the chlorine-containing fluorinated hydrocarbons. Especially a process for producing intermediates used for the production of fluorinated alkanes in a commercial scale and at a reduced cost is eagerly required. Vic-dichloro-fluorinated alkenes having chlorine atoms bonded to the carbon atoms of the carbon-carbon unsaturation in the molecule and other fluorinated alkenes are used as intermediates for the production of the fluorinated alkanes. For example, there have been proposed a process for allowing 1,2-dichlorohexafluorocyclopentene to react with hydrogen in the presence of a palladium or nickel catalyst to yield 1,1,2,2,3,3-hexafluorocyclopentane in DE-A 3,735,467 and U.S. Pat. No. 5,084,199; a process for treating 1,2-dichlorohexafluorocyclopentene with a fluorinating agent such as a potassium fluoride to yield a fluorine-substituted compound in U.S. Pat. No. 3,024,290; and a process for allowing said fluorine-substituted compound to react with hydrogen in the presence of a palladium catalyst to yield 1,2,3,3,4,4,5,5-octafluorocyclopentane in Japanese Patent Application No. 5-88022.

As examples of the process for producing vic-dichloro-fluorinated alkene, there can be mentioned two processes, i.e., a process using a perchloro-olefin and a process using a perchloro-conjugated diene compound.

As an example of the process using a perchloro-olefin, a process has been proposed in J. Am. Chem. Soc., 67, 1235 (1945) wherein octachlorocyclopentene is allowed to react with a mixture of antimony trifluoride and antimonytrifluoro-dichloride to yield 1,2-dichlorohexafluorocyclopentene. However, the reaction involved in this process is stoichiometric, and thus an expensive reagent must be used in a salient amount, and the yield is low, i.e, about 50%.

As another example, a process has been proposed in DE-C 3,935,493 wherein octachlorocyclopentene is allowed to react with chlorine and hydrogen fluoride in the presence of antimony pentachloride to yield 1,2-dichlorohexafluorocyclopentene. It is described in this patent that the antimony pentachloride used is fluorinated by the action of hydrogen fluoride to pentavalent antimony fluoride which has a fluorinating action, and, simultaneously with the fluorination, trivalent antimony produced as a by-product during the fluorination reaction is reproduced into pentavalent antimony by the action of chlorine gas, and thus, the antimony compound can be repeatedly used, namely, the reaction can be conducted with a catalytic amount of the antimony compound, and the yield is high. However, octachlorocyclopentene used as the starting material is expensive, and has poor handling properties because it is solid under normal temperature and normal pressure. Therefore, this process is not beneficial for a commercial scale production.

A perchloro-conjugated diene compound, for example, hexachlorocyclopentadiene is liquid under normal temperature and normal pressure and has good handling properties, is used widely as an intermediate for the preparation of pharmaceuticals and pesticides, and is readily commercially available and inexpensive. Therefore hexachlorocyclopentadiene is expected as a raw material for the production of a vic-dichloro-fluorinated alkene such as 1,2-dichlorohexafluorocyclopentene. For example, there have been proposed a process wherein hexachlorocyclopentadiene is allowed to react with antimony pentafluoride to yield 1,2-dichlorohexafluorocyclopentene in U.S. Pat. No. 2,459,783, and a process wherein hexachlorocyclopentadiene is first reacted with hydrogen fluoride and then the reaction product is reacted with chlorine gas in the presence of a catalyzing amount of antimony pentachloride to yield 1,2-dichlorohexafluorocyclopentene in U.S. Pat. No. 2,449,233. However, the reaction involved in the former process using antimony pentafluoride is stoichiometric, and therefore, an expensive reagent must be used in a salient amount, and the yield is low, i.e., at most about 40%. The latter process, wherein hexachlorocyclopentadiene is first allowed to react with hydrogen fluoride by using a catalyzing amount of antimony pentachloride, and then allowed to react with chlorine gas, involves side-reactions and the intended 1,2-dichlorohexafluorocyclopentene is produced only to a negligible extent. This is in striking contrast to the process of DE-C 3,935,493 wherein 1,2-dichlorohexafluorocyclopentene is produced from octachlorocyclopentene.

DISCLOSURE OF THE INVENTION

In view of the foregoing, the inventors have conducted extensive researches and found that the reaction of hexachlorocyclopentadiene, which is liquid at normal temperature and pressure and is inexpensive, with chlorine gas in the presence of a catalyzing amount of antimony pentachloride, and then with hydrogen fluoride gives 1,2-dichlorohexafluorocyclopentene in good yield, that the reaction of the thus-obtained 1,2-dichlorohexafluorocyclopentene with hydrogen using a palladium catalyst in the presence of triethylamine readily gives 1,1,2,2,3,3-hexafluorocyclopentane, and further that, when the 1,2-dichlorohexafluorocyclopentene is reacted with potassium fluoride to substitute the chlorine atoms to fluorine atoms, and then the reaction product is reacted with hydrogen in the presence of a palladium catalyst, 1,2,3,3,4,4,5,5-octafluorocyclopentane is readily obtained. Based on these findings, the present invention has been completed.

In accordance with the present invention, there are provided (1) a process for producing a vic-dichloro-fluorinated alkene represented by the following formula:

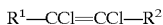

which comprises allowing a perchloro-conjugated diene compound to react with chlorine in the presence of an antimony catalyst, and then allowing the reaction product to react with hydrogen fluoride;

(2) a process for producing a fluorinated alkane represented by the following formula:

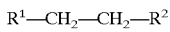

which comprises allowing a perchloro-conjugated diene compound to react with chlorine in the presence of an antimony catalyst, allowing the reaction product to react with hydrogen fluoride, and then allowing the thus-prepared vic-dichloro-fluorinated alkene to react with hydrogen in the presence of a hydrogenation catalyst and in the co-presence of a basic compound; and (3) a process for producing a fluorinated alkane represented by the following formula:

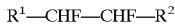

which comprises allowing a perchloro-conjugated diene compound to react with chlorine in the presence of an antimony catalyst, allowing the reaction product to react with hydrogen fluoride, allowing the thus-prepared vic-dichloro-fluorinated alkene to react with a fluorinating agent to substitute the chlorine atoms of the vic-dichloro-fluorinated alkene to fluorine atoms, and then allowing the thus-prepared fluorinated alkene to react with hydrogen in the presence of a hydrogenation catalyst.

BEST MODE FOR CARRYING OUT THE INVENTION

In the above-recited formulae, each of $R^1$ and $R^2$ independently represents a perfluoroalkyl group or both of $R^1$ and $R^2$ form together a perfluoroalkylene group. The number of carbons in each of $R^1$ and $R^2$ is not particularly limited, but is usually not larger than 20, preferably 1 to 10, and more preferably 1 to 4. As specific examples of the perfluoroalkyl group, there can be mention trifluoromethyl, pentafluoroethyl, heptafluoropropyl, heptafluoroisopropyl, nonafluorobutyl, nonafluoroisobutyl, undecafluoropentyl, tridecafluorohexyl, heptadecafluorooctyl, perfluorododecyl, perfluorotetradecyl, perfluorohexadecyl and perfluorooctadecyl. As specific examples of the perfluoroalkylene group, there can be mentioned, difluoromethylene, tetrafluoroethylene, hexafluoropropylene, octafluorobutylene, decafluoropentylene and dodecafluorohexylene. $R^1$ and $R^2$ should not be construed to mean limitedly only to these examples.

The main feature of the present invention lies in a reaction route wherein a perchloro-conjugated diene compound is first allowed to react with chlorine in the presence of an antimony catalyst, and then the reaction product is allowed to react with hydrogen fluoride. If hexachlorocyclopentadiene, which is a perchloro-conjugated diene compound, is first allowed to react with hydrogen fluoride, and then the reaction product is allowed to react with chlorine as described in U.S. Pat. No. 2,449,233, then salient amounts of by-products are produced and the intended 1,2-dichlorohexafluorocyclopentene is produced only in a limited amount. If a perchloro-conjugated diene compound is allowed to react with hydrogen fluoride and chlorine at the same time, similarly salient amounts of by-products are produced and the intended 1,2-dichlorohexafluorocyclopentene is produced only in a limited amount.

The present invention will now be described in detail.

The perchloro-conjugated diene compound used in the present invention is not particularly limited, and includes, for example, aliphatic perchloro-compounds such as hexachlorobutadiene, octachloropentadiene, decachlorohexadiene and tetradecachlorooctadiene, and alicyclic perchloro-compound such as hexachlorocyclopentadiene, octachlorocyclohexadiene, and dodecachlorocyclooctadiene. Of these, hexachlorobutadiene and hexachlorocyclopentadiene are preferably used. These perchloro-conjugated diene compounds can be easily produced in a large scale and a good yield by a process wherein a conjugated diene hydrocarbon compound such as cyclopentadiene is allowed to react with gaseous chlorine as described in, for example, GB Patent 1,070,891.

The antimony catalyst used in the present invention is not particularly limited, and those which are conventionally used for ordinary reactions can be used. As specific examples of the antimony catalyst, there can be mentioned anitmony fluorides such as antimony trifluoride and antimony pentafluoride, antimony chlorides such as antimony trichloride and antimony pentachloride, antimony mixed halides such as antimony trifluoro-dichloride, other antimony halides such as antimony tribromide and antimony triiodide, and antimony oxides such as antimony trioxide. Of these, antimony chlorides are preferable in view of enhanced catalyst activity and inexpensiveness. These catalysts may be used either alone or in combination.

The amount of the catalyst is not particularly limited, and varies depending upon the reaction conditions. The amount of the catalyst is usually 0.01 to 20 moles, preferably 0.1 to 10 moles and more preferably 0.5 to 5 moles, per mole of the perchloro-conjugated diene compound. If the amount of the catalyst is too small, the reaction time becomes unreasonably long and the degree of fluorination is lowered. In contrast, the use of an excessively large amount of catalyst is not advantageous for cost consideration. The antimony catalyst is very stable and is deactivated only to a negligible extent under the reaction conditions employed in the process of the invention, and, after the reaction product is removed by distillation, the catalyst can be successively reused merely by incorporating a starting compound.

A diluent can be used in the process of the present invention, if desired. The diluent used is not particularly limited provided that it is stable under the reaction conditions employed. As examples of the diluent, there can be mentioned aliphatic hydrocarbons such as n-pentane and n-hexane, alicyclic hydrocarbons such as cyclopentane and cyclohexane, aromatic hydrocarbons such as benzene and toluene, and perfluoroalkanes such as perfluorohexane, perfluoroheptane and perfluorodecalin. Of these, aliphatic hydrocarbons and alicyclic hydrocarbons are preferable. Instead of the perchloro-conjugated diene compound, intermediates for the intended vic-dichloro-fluorinated alkene derivatives can also be used, which include, for example, trichloropentafluorocyclopentene and tetrachlorotetrafluorocyclopentene.

The amount of gaseous chlorine, which is incorporated in a mixture of the starting compound, i.e., a perchloro-conjugated diene compound, and an antimony catalyst, is usually at least equimolar to the sum of the starting compound and the catalyst, and preferably 1 to 10 moles, more preferably 1 to 5 moles, per mole of the sum of the starting compound and the catalyst. However, when antimony pentachloride is used as the catalyst, the amount of gaseous chlorine should be at least equimolar to the starting compound. The reaction pressure is not higher than 10 kg/cm², preferably −0.5 to 6 kg/cm², as the gauge pressure. The reaction temperature may not necessarily be controlled, but, to ensure safety from heat evolved during the reaction and to prevent deterioration of the catalyst, the reaction temperature is usually controlled to a temperature of 20° to 200° C., preferably 60° to 150° C. and more preferably 80° to 120° C.

Hydrogen fluoride is not particularly limited provided that it can be used for ordinary chemical reactions, but, anhydrous hydrogen fluoride is preferably used to prevent hydrolysis of the catalyst and corrosion of an apparatus. The amount of hydrogen fluoride is usually at least 6 moles, preferably 6 to 20 moles, per mole of the starting compound.

The reaction conditions employed in the fluorination step are not particularly limited, but, since hydrogen chloride gas is evolved in this step, it is preferable for enhancing the reaction efficiency that an equipment provided with a reflux condensing cooling apparatus and a pressure-keeping valve is employed and the reaction pressure is maintained at a pressure higher than the vapor pressure of hydrogen fluoride to discharge hydrogen chloride gas from the reactor while avoiding the loss of hydrogen fluoride. The reaction pressure is usually in the range of 1 to 30 kg/cm², preferably 3 to 20 kg/cm² and more preferably 5 to 15 kg/cm². If the reaction pressure is too low, hydrogen fluoride is undesirably discharged and the degree of fluorination is reduced. In contrast, if the reaction pressure is too high, the removal of hydrogen chloride gas from the reaction system becomes difficult and the yield of the vic-dichloro-fluorinated alkene is lowered. The reaction temperature is usually in the range of 20° to 200° C., preferably 60° to 160° C. and more preferably 80° to 120° C. If the reaction temperature is too high, stability of the antimony catalyst is reduced. In contrast, if the reaction temperature is too low, the rate of reaction decreases. The reaction time varies depending upon the particular reaction pressure and reaction temperature, but is usually within 48 hours preferably in the range of 1 to 10 hours.

After the completion of evolution of hydrogen chloride gas, the residual hydrogen fluoride is removed and the reaction mixture can be aged. Namely, the pressure is restored to normal pressure and the reaction mixture is maintained at a reaction temperature of 20° to 200° C., preferably 60° to 160° C. and more preferably 80° to 140° C. The reaction time is usually within 20 hours and preferably 2 to 10 hours. When the reaction temperature is maintained at a temperature higher than the boiling point of the reaction product, usually in the range of 80° to 200° C., and preferably 120° to 140° C., distillation of the reaction product can be conducted simultaneously with proceeding of the reaction.

After the completion of reaction, the residual hydrogen fluoride is removed and the reaction mixture is distilled to give the intended reaction product. If desired, the product is fractionated thereby to be purified. The catalyst can be reused, and thus, after the removal of the reaction product by distillation, a raw material can be incorporated to repeat the reaction.

The thus-prepared vic-dichloro-fluorinated alkene is allowed to react with hydrogen by the conventional procedure using a hydrogenation catalyst in the presence of a basic compound to give a fluorinated alkane represented by the following formula:

wherein $R^1$ and $R^2$ are as defined above.

The basic compounds include organic basic compounds and inorganic basic compounds. As specific examples of the organic basic compounds, there can be mentioned organic carboxylic acid salts such as sodium formate, sodium acetate, potassium acetate, calcium acetate, sodium propionate, sodium butyrate and sodium valerate; carbonic acid salts such as sodium carbonate, potassium carbonate, lithium carbonate, magnesium carbonate, calcium carbonate, barium carbonate, sodium hydrogencarbonate and potassium hydrogencarbonate; and hydroxides such as sodium hydroxide, potassium hydroxide, calcium hydroxide, barium hydroxide and magnesium hydroxide. As specific examples of the inorganic basic compounds, there can be mentioned aliphatic amines such as ethylamine, diethylamine, ethanolamine, diethanolamine, triethanolamine, trimethylamine, triethylamine and diisopropylethylamine; aromatic amines such as 2-lutidine, aniline, N-methylaniline, N,N-dimethylaniline and N,N-diethylaniline; and heterocyclic amines such as 4-dimethylaminopyridine, pyridine, piperidine, pyrrolidine, N-methylpiperidine, N-methylmorpholine and N-ethylmorpholine. Among the inorganic basic compounds, alkali metal salts of organic carboxylic acids, alkali metal salts of carbonic acid and alkali metal hydroxides are preferable. Alkali metal hydroxides are most preferable. Among the organic basic compounds, aliphatic amines and heterocyclic amines are preferable. Aliphatic amines are most preferable. The amount of the basic compound is not particularly limited and varies depending upon the particular reaction conditions. Usually the amount of the basic compound is at least one mole, preferably 1 to 10 moles and more preferably 1 to 5 moles, per mole of the alcohol used.

The hydrogenation catalyst used is not particularly limited, and includes heterogeneous catalysts and homogeneous catalysts, which are conventionally used for hydrogenation of alkenes. As examples of the heterogeneous catalysts, there can be mentioned solid catalyst comprised of a metal of group 8 of the periodic table such as nickel, palladium or platinum, and solid catalyst comprised of a metal of group 8 of the periodic table, supported on a support such as carbon, silica, diatomaceous earth, alumina or titanium oxide. The solid catalyst includes, for example, those which are a combination of a nickel or cobalt compound with an organic compound of a metal of group 1 to 3 of the periodic table, such as nickel naphthenate/triethyl-aluminum, nickel octenoate/n-butyllithium and nickel acetyl-acetonate/triethyl aluminum. In the case where the hydrogenation product is purified by distillation immediately after completion of the hydrogenation reaction, a heterogeneous catalyst is preferably used because it can easily be separated. The amount of the catalyst is suitably selected within the range of $10^{-6}$ to 10% by weight, preferably $10^{-5}$ to $10^{31\ 2}$% by weight, based on the weight of the vic-dichloro-fluorinated alkene.

If desired, a solvent can be used as a reaction medium in the hydrogenation reaction. The solvent is not particularly limited provided that it is inert to the reaction. As specific examples of the solvent, there can be mentioned alcohols such as ethanol, methanol and isopropanol; aliphatic hydrocarbons such as n-pentane and n-hexane; alicyclic hydrocarbons such as cyclopentane and cyclohexane; esters such as ethyl acetate and butyl acetate; ethers such as diethyl ether, tetrahydrofuran and 1,4-dioxane; and ketones such as methyl ethyl ketone.

The reaction conditions are not particularly limited and vary depending the particular raw materials and reaction apparatus employed. Usually the reaction temperature is 0° to 200° C. and preferably 20° to 150° C., and the reaction time is 0.1 to 15 hours and preferably 0.5 to 10 hours. Although the reaction pressure varies depending upon the particular raw materials and the reaction temperature, usually the hydrogenation reaction is carried out at a pressure of about 1 to 50 kg/cm$^2$ in a closed reaction vessel.

After the completion of the hydrogenation reaction, the hydrogenation catalyst used is removed from the liquid reaction mixture and the liquid reaction mixture is distilled whereby a fluorinated alkane can be isolated.

The vic-dichloro-fluorinated alkene is allowed to react with a fluorinating agent by the conventional procedure to substitute the chlorine atoms of the vic-dichloro-fluorinated alkene by fluorine atoms, and then the thus-prepared fluorinated alkene is allowed to react with hydrogen in the presence of a hydrogenation catalyst to give a fluorinated alkane represented by the following formula:

$$R^1\text{—CHFCHF—}R^2$$

wherein $R^1$ and $R^2$ are as defined above.

The fluorinating agent used is not particularly limited and includes those which are conventionally used for substituting the chlorine atoms or bromine atoms of an alkane or alkene by fluorine atoms. As specific examples of the fluorinating agent, there can be mentioned alkali metal fluorides such as lithium fluoride, sodium fluoride, potassium fluoride, cesium fluoride and rubidium fluoride. Of these, potassium fluoride and cesium fluoride are preferable. The amount of the fluorinating agent is usually at least one mole, preferably 1 to 10 moles and more preferably 1 to 5 moles, per mole of the starting vic-dichloro-fluorinated alkene. If desired, a solvent can be used in the reaction medium in the fluorinating reaction. As specific examples of the solvent, there can be mentioned acid amides such as formamide, acetamide, dimethylformamide, dimethylacetamide and N-methylpyrrolidone, and sulfoxides such as dimethylsulfoxide and diethylsulfoxide. If desired, a compatible hydrocarbon such as xylene can be added to the solvent used. The reaction temperature is usually not higher than 200° C., preferably in the range of 60° to 180° C. and more preferably 80° to 140° C., and the reaction time is suitably selected depending upon the particular fluorinating agent and is usually within 24 hours.

The hydrogenation of the fluorinated alkene and the isolation of the resulting fluorinated alkane can be conducted by the same procedures as mentioned above.

The invention will now be specifically described by the following examples that by no means limit the scope of the invention.

EXAMPLE 1

A 0.7 liter-volume stainless steel reactor provided with a cooling reflux condenser and a pressure-keeping valve was charged with 95 g of antimony pentachloride and 33 g of hexachlorocyclopentadiene, and 10 g of chlorine gas was introduced at a pressure of 5 kg/cm$^2$ and a temperature of 80° C. to conduct chlorination for 2 hours. After the residual chlorine gas was discharged, 21 g of anhydrous hydrogen fluoride was added to conduct fluorination at 84° C. and 7 kg/cm$^2$ while hydrogen chloride gas produced is discharged through the pressure-keeping valve. After the completion of evolution of hydrogen chloride gas, the pressure was lowered to normal pressure and the residual hydrogen fluoride was removed, and the reaction was continued at 140° C. and normal pressure further for 5 hours. During the reaction, a fraction boiling at 70° to 110° C. was collected and neutralized with aqueous sodium bicarbonate to give 29.5 g of a crude product. Gas chromatography analysis of the product revealed that 28 g to the intended 1,2-dichlorohexachloropentene was obtained (yield: 95%).

Comparative Example 1

The same procedures as described in Example 1 were repeated except that the order of application of the reactants was changed, i.e., hexachlorocyclopentadiene was allowed to first react with hydrogen fluoride and then react with chlorine. The intended 1,2-dichlorohexachloropentene was obtained only in a negligible amount, and, 41% of 1,2,4-trichloro-3,3,5,5-tetrafluorocyclopentene and 33% of an mixture of trifluoro-isomers were obtained as by-products.

Comparative Example 2

The same procedures as described in Example 1 were repeated except that chlorine gas and hydrogen fluoride were simultaneously charged into the reactor and, after the reactor was closed, a reaction was conducted at 150° C. The intended 1,2-dichlorohexachloropentene could not be obtained, and, 16.1% of a tetrafluoro-isomer mixture, 35.6% of a trifluoro-isomer mixture and 35.6% of a difluoro-isomer mixture were obtained as by-products.

EXAMPLE 2

In this example, a catalyst was repeatedly used.

First use

A 0.7 liter-volume stainless steel reactor provided with a cooling reflux condenser and a pressure-keeping valve was charged with 95 g of antimony pentachloride and 140 g of hexachlorocyclopentadiene, and 39 g of chlorine gas was introduced at a pressure of 5 kg/cm$^2$ and a temperature of 80° C. to conduct chlorination for 2 hours. Then, 210 g of anhydrous hydrogen fluoride was added to conduct fluorination at 100° C. and 10 kg/cm$^2$ while hydrogen chloride gas produced is discharged through the pressure-keeping valve. After the completion of hydrogen chloride gas, the pressure was lowered to normal pressure and the residual hydrogen fluoride was removed, and the reaction was continued at 140° C. and normal pressure further for 5 hours. During the reaction, a fraction boiling at 70° to 110° C. was collected and neutralized with aqueous sodium bicarbonate to give 127 g of a crude product. Gas chromatography analysis of the product revealed that 107.5 g (yield, 86%) of the intended 1,2-dichlorohexachloropentene was obtained.

Second use

Into the reactor containing the distillation residue, 140 g of hexachlorocyclopentadiene was newly added and the reaction was conducted by the same procedures as described above with respect to the first use of the catalyst. 101.7 g of a crude product and 93.3 g (yield, 74%) of the intended 1,2-dichlorohexachloropentene were obtained. Thus it was found that the catalyst was deactivated only to a small extent during the second use, and could repeatedly be used.

EXAMPLE 3

The same procedures as described in Example 1 were repeated except that hexachlorobutadiene was used instead of hexachlorocyclopentadiene. The intended 2,3-dichlorohexafluoro-2-butene was obtained in a good yield.

EXAMPLE 4

A 1 liter-volume reactor was charged with 23.2 g of potassium fluoride and 400 ml of N-methylpyrrolidone, and the content was heated to 200° C. 24.5 g of 1,2-dichlorohexafluorocyclopentene obtained in Example 1 was added dropwise over a period of 3 hours, and the mixture was maintained at 200° C. for 8 hours to conduct distillation to give 14.9 g (yield, 70%) of octafluorocyclopentene (b.p., 27° C.).

Then a reactor was charged with 12 g of the octafluorocyclopentene and 0.24 g of a 5%-palladium/carbon catalyst and hydrogenation was conducted at a temperature of 50° C. and a hydrogenation pressure of 6 kg/cm². When the absorption of hydrogen ceased, the reaction was completed. After the removal of the catalyst and the produced hydrogen fluoride from the reaction mixture, the reaction mixture was distilled to give 9 g of 1,2,3,3,4,4,5,5-octafluorocyclopentane (b.p., 79° C.; purity, 99%).

EXAMPLE 5

A stainless steel reactor, the inner wall of which was lined with a fluoroplastic, was charged with 5.0 g of 1,2-dichlorohexafluorocyclopentene, 0.1 g of a 5%-palladium/carbon catalyst and 4.1 g of triethylamine, and hydrogen gas was introduced to a pressure of 5 kg/cm². The mixture was heated to 40° C. while being stirred, and the reaction was conducted while the hyfrogen consumed was supplemented. After 7 hours' reaction, it was confirmed that the consumption of hydrogen ceased. Then the catalyst was removed from the reaction mixture and the reaction mixture was distilled to give 4.2 g of 1,1,2,2,3,3-hexafluorocyclopentane (b.p., 84.5–85° C. ).

INDUSTRIAL APPLICABILITY

By the practice of the present invention, a perchloroconjugated diene compound such as hexachlorocyclopentadinene, which is liquid at normal temperature and pressure and is inexpensive, can be converted to a corresponding vic-dichlorofluorinated alkene in a good yield and in a commercial scale. The vic-dichlorofluorinated alkene is either (i) hydrogenated, or (ii) is treated with a fluorinating agent to substitute the chlorine atoms to fluorine atoms, and then the thus-obtained fluorinated alkene is hydrogenated, whereby a fluorinated alkane can be obtained in a commercial scale.

The thus-obtained fluorinated alkenes and fluorinated alkanes are useful as substitutes for chlorine-containing fluorinated hydrocarbons or intermediates for the preparation thereof, and raw materials for the synthesis of pharmaceuticals, pesticides, liquid crystals and polymers.

We claim:

1. A process for producing a vic-dichloro-fluorinated alkene represented by the following formula:

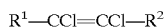

wherein each of $R^1$ and $R^2$ independently represents a perfluoroalkyl group or both of $R^1$ and $R^2$ form together a perfluoroalkylene group, characterized by the steps of:
allowing a perchloro-conjugated diene compound to react with chlorine in the presence of an antimony catalyst and in the absence of hydrogen fluoride, and then
allowing the reaction product to react with hydrogen fluoride.

2. A process for producing the vic-dichloro-fluorinated alkene according to claim 1, wherein, after completion of the reaction with hydrogen fluoride, an excessive amount of hydrogen fluoride is removed from the reaction mixture and the reaction product is distilled off, and thereafter, a perchloro-conjugated diene compound is newly added to the distillation residue to successively repeat the reactions for the production of the vic-dichloro-fluorinated alkene.

3. A process for producing the vic-dichloro-fluorinated alkene according to claim 1, wherein the chlorination reaction is conducted at a temperature of 20° to 200° C. and a pressure not higher than 10 kg/cm².

4. A process for producing the vic-dichloro-fluorinated alkene according to claim 1, wherein the reaction with hydrogen fluoride is conducted at a temperature equal to or higher than the boiling point of the reaction product.

5. A process for producing the vic-dichloro-fluorinated alkene according to claim 1, wherein the reaction with hydrogen fluoride is conducted at a temperature of 20° to 200° C.

6. A process for producing the vic-dichloro-fluorinated alkene according to claim 1, wherein the perchloro-conjugated diene compound is hexachlorobutadiene or hexachlorocyclopentadiene.

7. A process for producing the vic-dichloro-fluorinated alkene according to claim 1, wherein the amount of the antimony catalyst is in the range of 0.01 to 20 moles per mole of the perchloro-conjugated diene compound.

8. A process for producing the vic-dichloro-fluorinated alkene according to claim 1, wherein the antimony catalyst is an antomony halide.

9. A process for producing the vic-dichloro-fluorinated alkene according to claim 8, wherein the antimony halide is antimony chloride.

10. A process for producing the vic-dichloro-fluorinated alkene according to claim 1, wherein the hydrogen fluoride is anhydrous hydrogen fluoride.

11. A process for producing a fluorinated alkane represented by the following formula:

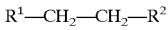

wherein each of $R^1$ and $R^2$ independently represents a perfluoroalkyl group or both of $R^1$ and $R^2$ form together a perfluoroalkylene group, characterized by the steps of:
allowing a perchloro-conjugated diene compound to react with chlorine in the presence of an antimony catalyst and in the absence of hydrogen fluoride,
allowing the thus-prepared reaction product to react with hydrogen fluoride to give a vic-dichlorofluorinated alkene represented by the follow formula:

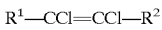

wherein $R^1$ and $R^2$ are as defined above, and then
allowing the vic-dichloro-fluorinated alkene to react with hydrogen in the presence of a hydrogenation catalyst and in the co-presence of a basic compound.

12. A process for producing the fluorinated alkane according to claim 11, wherein, after completion of the reaction of the reaction product prepared in the first step with hydrogen fluoride, an excessive amount of hydrogen fluoride is removed from the reaction mixture and the reaction product is distilled off, and thereafter, a perchloro-conjugated diene compound is newly added to the distillation residue to successively repeat the reactions for the production of the vic-dichloro-fluorinated alkene.

13. A process for producing the fluorinated alkane according to claim 11, wherein the perchloro-conjugated diene compound is hexachlorocyclopentadiene or hexachloropentadiene.

14. A process for producing the fluorinated alkane according to claim 11, wherein the basic compound is an amine compound or a basic alkali metal salt.

15. A process for producing the fluorinated alkane according to claim 11, wherein the hydrogenation catalyst is heterogeneous catalyst or a homogeneous catalyst.

16. A process for producing the fluorinated alkane according to claim 11, wherein the hydrogenation catalyst is heterogeneous catalyst.

17. A process for producing the fluorinated alkane according to claim 16, wherein the heterogeneous catalyst is a catalyst of a metal selected from the group consisting of metals of group 8 of the periodic table.

18. A process for producing a fluorinated alkane represented by the following formula:

$$R^1-CHF-CHF-R^2$$

wherein each of $R^1$ and $R^2$ independently represents a perfluoroalkyl group or both of $R^1$ and $R^2$ form together a perfluoroalkylene group, characterized by the steps of:

allowing a perchloro-conjugated diene compound to react with chlorine in the presence of an antimony catalyst and in the absence of hydrogen fluoride, allowing the thus-prepared reaction product to react with hydrogen fluoride to give a vic-dichloro-fluorinated alkene represented by the following formula:

$$R^1-CCl=CCl-R^2$$

wherein $R^1$ and $R^2$ are as defined above, allowing the vic-dichloro-fluorinated alkene to react with a fluorinating agent to substitute the chlorine atoms of the vic-dichloro-fluorinated alkene by fluorine atoms, and then allowing the thus-prepared fluorinated alkene to react with hydrogen in the presence of a hydrogenation catalyst.

19. A process for producing the fluorinated alkane according to claim 18, wherein, after completion of the reaction of the reaction product prepared in the first step with hydrogen fluoride, an excessive amount of hydrogen fluoride is removed from the reaction mixture and the reaction product is distilled off, and thereafter, a perchloro-conjugated diene compound is newly added to the distillation residue to successively repeat the reactions for the production of the vic-dichloro-fluorinated alkene.

20. A process for producing the fluorinated alkane according to claim 18, wherein the perchloro-conjugated diene compound is hexachlorobutadiene or hexachlorocyclopentadiene.

21. A process for producing the fluorinated alkane according to claim 18, wherein the fluorinating agent is an alkali metal fluoride.

22. A process for producing the fluorinated alkane according to claim 18, wherein the hydrogenation catalyst is heterogeneous catalyst or a homogeneous catalyst.

23. A process for producing the fluorinated alkane according to claim 22, wherein the hydrogenation catalyst is heterogeneous catalyst.

24. A process for producing the fluorinated alkane according to claim 23, wherein the heterogeneous catalyst is a catalyst of a metal selected from the group consisting of metals of group 8 of the periodic table.

* * * * *